United States Patent [19]

Hill

[11] 4,362,731
[45] Dec. 7, 1982

[54] MYOTONOLYTIC USE OF 4,5,6,7-TETRAHYDROISOXAZOLO [5,4-C] PYRIDIN-3-OL AND DERIVATIVES THEREOF

[75] Inventor: Ronald C. Hill, Muttenz, Switzerland

[73] Assignee: Sandoz Ltd., Basel, Switzerland

[21] Appl. No.: 296,327

[22] Filed: Aug. 26, 1981

[30] Foreign Application Priority Data

Sep. 1, 1980 [GB] United Kingdom ............... 8028199

[51] Int. Cl.$^3$ .................... A61K 31/44; A61K 31/435
[52] U.S. Cl. .................................... 424/256; 424/263
[58] Field of Search ................................ 424/256, 263

[56] References Cited
PUBLICATIONS

Chem. Abst., vol. 92-157832v (1980).

*Primary Examiner*—Stanley J. Friedman
*Attorney, Agent, or Firm*—Gerald D. Sharkin; Robert S. Honor; Joseph J. Borovian

[57] ABSTRACT

The myotonolytic use of compounds of formula I

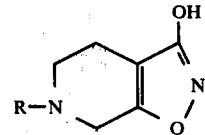

wherein R is hydrogen, acetyl or a group of formula II

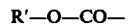

R'—O—CO—     II wherein R' is alkyl($C_{1-8}$); phenyl; phenyl substituted in the 4-position with halogen, alkoxy($C_{1-4}$) or alkyl($C_{1-4}$); phenylalkyl; or phenylalkyl in which the phenyl group is substituted in the 4-position with halogen, alkoxy($C_{1-4}$) or alkyl($C_{1-4}$).

8 Claims, No Drawings

MYOTONOLYTIC USE OF 4,5,6,7-TETRAHYDROISOXAZOLO [5,4-C] PYRIDIN-3-OL AND DERIVATIVES THEREOF

The present invention relates to a novel pharmaceutical use for the compounds of formula I

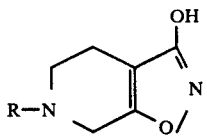

wherein R is hydrogen, acetyl or a group of formula II

wherein R' is alkyl($C_{1-8}$); phenyl; phenyl substituted in the 4-position with halogen, alkoxy($C_{1-4}$) or alkyl($C_{1-4}$); phenylalkyl; or phenylalkyl in which the phenyl group is substituted in the 4-position with halogen, alkoxy($C_{1-4}$) or alkyl($C_{1-4}$).

The compounds of formula I may also exist as zwitterions of formula Ia and tautomers of formula Ib:

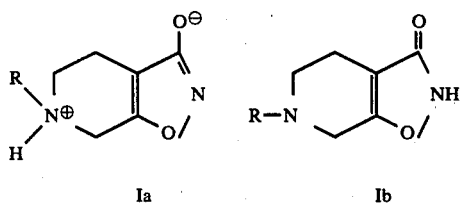

For the sake of convenience formula I as used herein is to be understood as including both the zwitterion and tautomeric forms of formula Ia and Ib as well as mixtures thereof and references to formula I as well as to individual compounds of formula I throughout the specification and claims are to be construed accordingly.

The compounds of formula I as well as processes for their production are known e.g. from European patent application No. 78 100 191.2 filed June 19th, 1978 and published Jan. 24th, 1979 (publication No. 338).

These compounds are known to possess γ-aminobutyric acid (GABA) related activity and are indicated for use in treating GABA system malfunction-related diseases, e.g. neurological and psychiatric disorders such as epilepsy, parkinsonism, schizophrenia, Huntington's chorea, diseases involving malfunction of the pituitary hormones, and cerebral arteriosclerosis.

In accordance with the present invention it has now surprisingly been found that the compounds of formula I also exhibit myotonolytic activity as may be demonstrated in standard animal tests, e.g. as hereinafter described.

The compounds of formula I are therefore useful in the treatment of myotonic conditions (e.g. in inducing muscle relaxation or in treating muscle spasm or muscular spasticity) and may be administered to treat muscle spasm or muscular spasticity as a component of, for example, tension headache, cerebral palsy, tardive dyskinesia, hemiplegia and muscular rheumatism.

The present invention accordingly provides a method of treating myotonic conditions in a subject in need of such treatment, which method comprises administering to said subject a myotonolytically effective amount of a compound of formula I as hereinabefore defined.

The preferred compound for use in accordance with the method of the invention is the compound of formula I wherein R is hydrogen, namely 4,5,6,7-tetrahydroisoxazolo[5,4-c]pyridin-3-ol, hereinafter referred to as THIP.

The compounds of formula I when not in zwitterion form may be administered in free form or in the form of their pharmaceutically acceptable acid addition salts or pharmaceutically acceptable salts with bases. Such salt forms are also known and include for example the hydrochloride and the metal salts, e.g. the sodium salt.

The activity of such pharmaceutically acceptable salt forms will generally be of the same order as that of the respective free compound form. Though the use of the compounds in free form is generally preferred, the use of pharmaceutically acceptable salt forms is also to be understood as falling within the purview of the present invention, and the claims are to be interpreted accordingly.

As used herein all amounts for the formula I compounds recited refer to the amount of the free form. The same applies to weight ratios.

The compounds of formula I, e.g. THIP, are useful as myotonolytics as indicated in standard animal tests, for example in accordance witgh the following methods.

(a) Inhibition of Thalamonal-induced rigor in the rat:

Rigor is induced in male and female rats (Sprague Dawley strain: 160–200 g) by the administration of 7.5 mg/kg of Thalamonal (2.5 mg/ml droperidol and 0.5 mg/ml fentanyl). After 15 minutes each test animal is immobilized in a hammock and bipolar electrode inserted into the calf muscle of one limb. The electromyogram is recorded on a Beckman Dynograph. Thirty minutes after administration of the Thalamonal, the test compund is administered by i.v. injection into the tail vein in increasing doses at 10 minute intervals. Six rats are used per compound and the dose necessary to reduce the intensity of the rigor by 10% (minimum effective dose=MED) and the dose required to completely abolish the rigor ($ED_{100}$) are determined by comparison of the integrated electromyograms obtained before and after the administration of the test compound.

In the above test compounds of the formula I, e.g. THIP, were found to be active at doses of from about 0.007 to about 15 mg/kg i.v. The MED and $ED_{100}$ for THIP were found to be 0.007 mg/kg i.v. and 4.2 mg/kg i.v. respectively, (MED and $ED_{100}$ values found in this test for the compound Kiazepam, known for use as a myotonolytic, are 0.011 mg/kg i.v. and 2.2 mg/kg i.v. respectively).

(b) Effect on muscle-tone in the rabbit;

The method used is based on that described by Teschendorf et al. [Naunyn-Schmiedeberg's Arch. Pharmacol. 266, 467 (1970)], employing Thüringer rabbits of either sex (weight range 2.0–2.5 kg). The conscious animal is placed on its back between foam-rubber blocks and strapped into position with the right handpaw fixed to a vertical hinged arm. A bipolar electrode is inserted into the right gastrocnemius muscle in the same leg and muscle activity displayed on an oscillograph.

The apparatus is programmed such that an eccentric disc revolves once every five minutes (time of rotation=3 seconds), urging the hinged arm forward to induce reflex muscle activity in the gastrochemius muscle (tonic stretch reflex). The potentials arising during each 3-second period are recorded by digital counter, the input sensitivity of which is so adjusted that stray potentials arising during the resting period are disregarded.

Before injection of the first dose of the test compound a 1-hour adaptation period is allowed during which the tonic stretch reflex is elicited at 5-minute intervals. The mean of the last 5 recordings during the adaptation period is calculated and the post-treatment values are each expressed as a percentage of this mean. The test compound is injected i.v. in increasing doses at hourly intervals and the maximum effect of each dose (lowest number of potentials arising during elicitation of the tonic stretch reflex) used to construct a dose-response curve, from which the $ED_{50}$ is calculated by regression analysis. 2 to 10 animals are used per test compound at each of the test dosages.

In the above test, compounds of the formula I, e.g. THIP, were found to be active at doses of from about 0.5 to 10 mg/kg i.v. The $ED_{50}$ for THIP was found to be 1.05 mg/kg i.v. ($ED_{50}$ found in this test for Diazepam = 0.23 mg/kg i.v.).

(c) Effect on climbing behaviour in the mouse:

The method used is based upon that described by Kniep [Arch. Int. Pharmacodyn. Therapie, 126, 238 (1960)]. In this method the test substance is administered s.c. to male mice of the OFA strain and weighing 20–28 g. One hour after administration the mice are placed in a transparent, plexiglass cylinder of 26 cm diameter and 40 cm high, having a wire mesh grid placed at an angle of 45° across half of the bottom of the cylinder. The number of climbing acts from the floor onto the grid are counted for each mouse separately during the 10 minute period immediately following. A climbing act is considered to have occurred when an animal places all four paws on the grid. Ten mice, divided into two groups of five, are used per dose and the $ED_{50}$, estimated by half-log regression analysis, is taken as the dose which reduces the total number of climbing acts by 50% compared to animals treated with solvent only.

Compounds of the formula I, e.g. THIP, were found to be active in the above test at doses of from about 1 to about 10 mg/kg i.p. The $ED_{50}$ for THIP was found to be 4.0 mg/kg i.p. ($ED_{50}$ found in this test for Diazepam = 5.6 mg/kg i.p.).

The compound THIP is physiologically tolerated, for example over periods of 14 days administered at a dosage of 60 mg/kg p.o. in rats and at a dosage of 20 mg/kg/day p.o. in dogs and baboons. The $LD_{50}$ for THIP is 70 mg/kg i.v. and 195 mg/kg p.o., in the mouse. The tolerability of other compounds of formula I is of the same order as that of THIP.

The compounds of the invention, in particular the compound THIP, also have the advantage over other compounds known for myotonolytic use, e.g. belonging to the benzodiazepine class, of not supporting physical dependency. This may be demonstrated e.g. in the single dose suppression test in morphine dependent rhesus monkeys, conducted e.g. as follows: 4 male, morphine-dependent rhesus monekys weighing 3.2–4.5 kg are each kept in a metal harness (weight 600 g), in separate, open-fronted cubicles (70×70×90 cm) with free access to food and water, and with a maintained 12 hour light-day cycle (6 a.m.–6 p.m. light). After 7 days acclimatisation to their harnesses and to the cages, the monkeys are anaesthetised with pentothal i.v. and halothane and implanted with a single-lumen catheter into the left jugular vein. The free end of the catheter is then led subcutaneously over the shoulder of each animal and out through a small stab wound made in the skin between the shoulder blades. The monkeys are refitted into their harnesses and connected to a saline-filled cannula leading from injection pumps. During the 7-day recovery period the monkeys receive 0.8 ml physiological saline through the outer canula every 30 minutes in order to keep the tip of the cannula in the jugular vein free of clots. Thereafter each monkey receives programmed injections of morphine, two monkeys at dosages of 3.2 mg/kg, 6 times daily and two at 5.6 mg/kg, 6 times daily, administration being effected at intervals of 4 hours for a period of from 33–46 weeks. Sixteen hours after the last injection of morphine, each monkey receives an intravenous injection of one dose of test compound and the degree to which the morphine withdrawal syndrome is suppressed is recorded at 30 minute intervals until the symptoms have returned to the pre-treatment level.

The compound THIP was found to have no effect on the severity or duration of morphine withdrawal syndrome when administered at dosages of 1 and 3.2 mg/kg i.v. to monkeys previously receiving individual morphine dosages of both 3.2 and 5.6 mg/kg.

Clinical trials suitable for demonstrating myotonolytic effectiveness of compounds of formula I may be conducted with patients exhibiting e.g. (i) spasticity consequent to cerebral and/or spinal lesion and (ii) cerebral paresis, as trial subjects. Suitable clinical trial programmes are as follows:

1. For subjects exhibiting spasticity consequent to cerebral and/or spinal lesion:

Test compound, e.g. THIP, is administered to individual trial subjects per orally at a dosage of from 15 to 40 mg. To determine myotonolytic effectiveness of the dosage the following parameters are determined in accordance with standard techniques:

T-reflex (Achilles' tendon reflex)
Resistance to passive extension (tonus-catch)
Flexor reflex (threshold)
Muscle force
Clonus All subjects are submitted to a full clinical examination before and after completion of the trial and blood-pressure and pulse are measured continuously during the trail period. All side-effects of any degree are recorded.

2. For subjects exhibiting cerebral paresis:

Test compound, e.g. THIP, is administered to individual trial subjects per orally at an initial daily dosage rate of 3×2.5 mg and the daily dosage rate is increased on consecutive or alternate days by 2.5 mg/day at each increase. During this phase observations are made for the following parameters:

Gait
Resistance to passive extension (tonus-catch)
Muscle force
Clonus
Reflex zones (crossed adduction)

Increase of dosage rate is continued until a maximum therapeutic effect is observed or until occurrence of side-effects and at all events not beyond a maximum daily dosage of 3×30 mg. Once the maximum therapeutic dosage is established for individual test subjects, this is maintained constant for a period of ca. 7 days, with continued observation for the recited parameters. During the trials the subjects are maintained free of other myotonolytic medication, in particular of benzodiazepine therapy and, as far as possible, of any other medication. Methorale is administered to treat any occurrence of sleep disturbance and the occurrence of all side-effects is recorded.

The amount of compound administered in practicing the method of the invention will of course vary according to e.g. the particular compound employed, the mode of administration, the condition to be treated and the therapy desired.

In general satisfactory results are obtained using the compounds of formula I, e.g. THIP, at a dailydose of from about 0.2 to about 40 mg/kg. Conveniently the compound is presented in unit dosage form administered once or 2 to 4 times a day or in sustained release form. A suitable daily dosage regimen for patients requiring myotonolytic therapy is for example as described above for clinical trial programmes. In general a suitable oral daily dosage is from about 4 to about 40 mg, preferably from about 5 to about 20 mg, and suitable unit dosage forms contain from about 1 to about 20 mg, preferably about 5 to about 10 mg of for example the compound THIP in association with a pharmaceutical carrier or diluent. Pharmaceutical compositions for use in the method of the invention may be prepared in accordance with standard techniques for example by admixture of the active ingredient with conventional pharmaceutically acceptable diluents or carriers and optionally other excipients. Suitable forms for administration include tablets, capsules and injectable solutions. Solid forms, in particular unit dosage forms, suitable for oral administration are preferred.

In addition to the foregoing the present invention also provides (i) a pharmaceutical composition comprising a compound of formula I as hereinbefore defined as active ingredient, for use in a method according to the present invention as well as (ii) a pack containing a pharmaceutical composition comprising a compound of formula I as hereinbefore defined as active ingredient, said pack being associated with instructions for the use of said composition in a method according to the present invention. The instructions may for example be physically associated with, e.g., printed upon, the pack.

The following examples illustrate compositions for use in accordance with the method of the invention.

EXAMPLE

Production of pharmaceutical compositions

Tablets may contain the active agent in admixture with conventional pharmaceutically acceptable excipients, e.g. inert diluents, such as microcrystalline cellulose, lactose and starch; disintegrating agents, e.g. starch, colloidal silicium dioxide and alginic acid; binding agents, e.g. gelatin and polyvinylpyrrolidone; lubricating agents, e.g. magnesium stearate, stearic acid and talc as well as flavouring, colouring and sweetening agents. The tablets may be uncoated or coated by known techniques to delay disintegration and absorption in the gastrointestinal tract and thereby provide a sustained action over a longer period.

For the manufacture of tablets, the compounds of formula I can be mixed with lactose and corn starch and granulated with aqueous polyvinylpyrrolidone or gelatine solution. The dried granulate is compressed into tablets in the presence of corn starch, silicium dioxide and magnesium stearate. In this way, there may be obtained, e.g. tablets of the following composition:

| Ingredients | 5 mg Tablet |
|---|---|
| Compound of formula I e.g. THIP | 5.0 mg |
| Lactose | 117.0 mg |
| Corn Starch | 14.0 mg |
| Polyvinylpyrrolidone | 3.0 mg |
| Silicium dioxide (colloidal) | 0.3 mg |
| Magnesium stearate | 0.7 mg |
| Total tablet weight | 140.0 mg |

These tablets may be administered orally in a dosage of e.g. one tablet two to four times per day. Capsules may contain the active agent alone or admixed with an inert solid diluent, for example as mentioned above.

Capsules containing the ingredients indicated below may be prepared by conventional techniques and are administered at a dosage of one capsule 2 to 4 times a day:

| Ingredients | 5 mg Capsule | 15 mg Capsule |
|---|---|---|
| Compound of formula I e.g. THIP as the hydrate | 5.0 mg | 15.0 mg |
| Corn starch | 135.9 mg | 131.9 mg |
| Lactose (200 mesh) | 203.85 mg | 197.85 mg |
| Silicium dioxide (Aerosil 200) | 1.75 mg | 1.75 mg |
| Magnesium stearate | 3.5 mg | 3.5 mg |
| Total content weight | 350.0 mg | 350.0 mg |
| Capsule weight | 97.0 mg | 97.0 mg |
| Total Capsule weight | 447.0 mg | 447.0 mg |

Solutions and suspensions may contain the compound of formula I as the active agent in admixture with any of the conventional excipients utilized for the preparation of such compositions, e.g. suspending agents, such as methylcellulose, tragacanth and microcrystalline cellulose; wetting agents, such as lecithin, polyoxyethylene stearate and polyoxyethylene sorbitan monoleate; flavouring, colouring and sweetening agents and preservatives, such as methyl-p-hydroxy-benzoate.

Such liquid preparations may be put up in the form of e.g. injectable or per-oral suspensions containing e.g. 5 and 10 mg active ingredient respectively and suitable for administration once or 2 to 4 times per day.

What we claim is:

1. A method of treating myotonic conditions in a subject in need of such treatment, which method comprises administering to said subject a myotonolytically effective amount of a compound of formula I

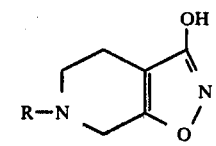

wherein R is hydrogen, acetyl or a group of formula II

R'—O—CO—    II wherein R' is alkyl($C_{1-8}$); phenyl; phenyl substituted in the 4-position with halogen, alkoxy ($C_{1-4}$) or alkyl($C_{1-4}$); phenylalkyl; or phenylalkyl in which the phenyl group is substituted in the 4-position with halogen, alkoxy($C_{1-4}$) or alkyl($C_{1-4}$).

2. A method according to claim 1, wherein the compound of formula I is 4,5,6,7-tetrahydroisoxazolo[5,4-c]pyridin-3-ol.

3. A method according to claim 1 of treating muscle spasm or muscular spasticity occurring as a component of tension headache, cerebral palsy, hemiplegia or muscular rheumatism.

4. A method according to claim 1, wherein the compound of formula I is administered at a daily dosage of from about 1 to about 40 mg.

5. A method according to claim 4, wherein the compound of formula I is administered at a daily dosage of from about 5 to about 20 mg.

6. A method according to claim 1, wherein the compound of formula I is administered orally in unit dosage form.

7. A method according to claim 6, wherein each unit dosage contains from about 1 to about 20 mg of the compound of formula I.

8. A method according to claim 7, wherein each unit dosage contains from about 5 to about 15 mg of the compound of formula I.

* * * * *